(12) United States Patent
Griffin et al.

(10) Patent No.: US 7,951,066 B2
(45) Date of Patent: May 31, 2011

(54) MEDICAL DEVICE POSITIONING ASSEMBLIES AND METHODS

(75) Inventors: Mark A. Griffin, Louisville, KY (US); Vas Abramov, Louisville, KY (US); Michael G. McGrath, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1108 days.

(21) Appl. No.: 11/207,127

(22) Filed: Aug. 17, 2005

(65) Prior Publication Data
US 2007/0043336 A1    Feb. 22, 2007

(51) Int. Cl.
*A61F 2/00* (2006.01)
(52) U.S. Cl. .......................................... 600/30; 600/29
(58) Field of Classification Search .................... 600/37, 600/29–30; *A61F 2/00, 2/02*
See application file for complete search history.

(56) References Cited

U.S. PATENT DOCUMENTS

| | | | |
|---|---|---|---|
| 5,174,910 A * | 12/1992 | Pita ............................... | 249/112 |
| 5,611,515 A | 3/1997 | Benderev et al. | |
| 5,746,763 A | 5/1998 | Benderev et al. | |
| 5,813,408 A | 9/1998 | Benderev et al. | |
| 5,836,314 A | 11/1998 | Benderev et al. | |
| 5,836,315 A | 11/1998 | Benderev et al. | |
| 5,860,425 A | 1/1999 | Benderev et al. | |
| 6,056,688 A | 5/2000 | Benderev et al. | |
| 6,077,216 A | 6/2000 | Benderev et al. | |
| 6,702,827 B1 * | 3/2004 | Lund et al. ..................... | 606/151 |
| 7,229,453 B2 * | 6/2007 | Anderson et al. ............. | 606/151 |
| 2001/0018549 A1 * | 8/2001 | Scetbon .......................... | 600/30 |
| 2003/0191360 A1 * | 10/2003 | Browning ....................... | 600/29 |
| 2005/0277807 A1 * | 12/2005 | MacLean et al. ............... | 600/30 |
| 2008/0132753 A1 * | 6/2008 | Goddard ......................... | 600/37 |
| 2008/0269548 A1 * | 10/2008 | Vecchiotti et al. ............. | 600/30 |

FOREIGN PATENT DOCUMENTS

| | | |
|---|---|---|
| EP | 0 677 297 | 10/1995 |
| WO | WO-98/35632 | 8/1998 |
| WO | WO-02/19945 | 3/2002 |
| WO | WO-03/007847 | 1/2003 |
| WO | WO-2004-060206 | 7/2004 |
| WO | WO 2004060206 A1 * | 7/2004 |
| WO | WO-2004-096088 | 11/2004 |

OTHER PUBLICATIONS

"Advantage Mid-Urethral Sling System," http://www.bostonscientific.com/med_specialty, (2004).

* cited by examiner

*Primary Examiner* — Charles A Marmor, II
*Assistant Examiner* — Catherine E Burk
(74) *Attorney, Agent, or Firm* — Bingham McCutchen LLP

(57) ABSTRACT

A medical retrieval device of an embodiment of the present disclosure includes an assembly for positioning a medical device includes a sleeve having a lumen configured to accept a medical device, and a tab. The tab includes a distal portion and a proximal portion. The distal portion is configured to receive the sleeve for positioning the sleeve proximate the proximal portion. The proximal portion is configured such that severing the tab along the proximal portion maintains the tab in one piece.

27 Claims, 16 Drawing Sheets

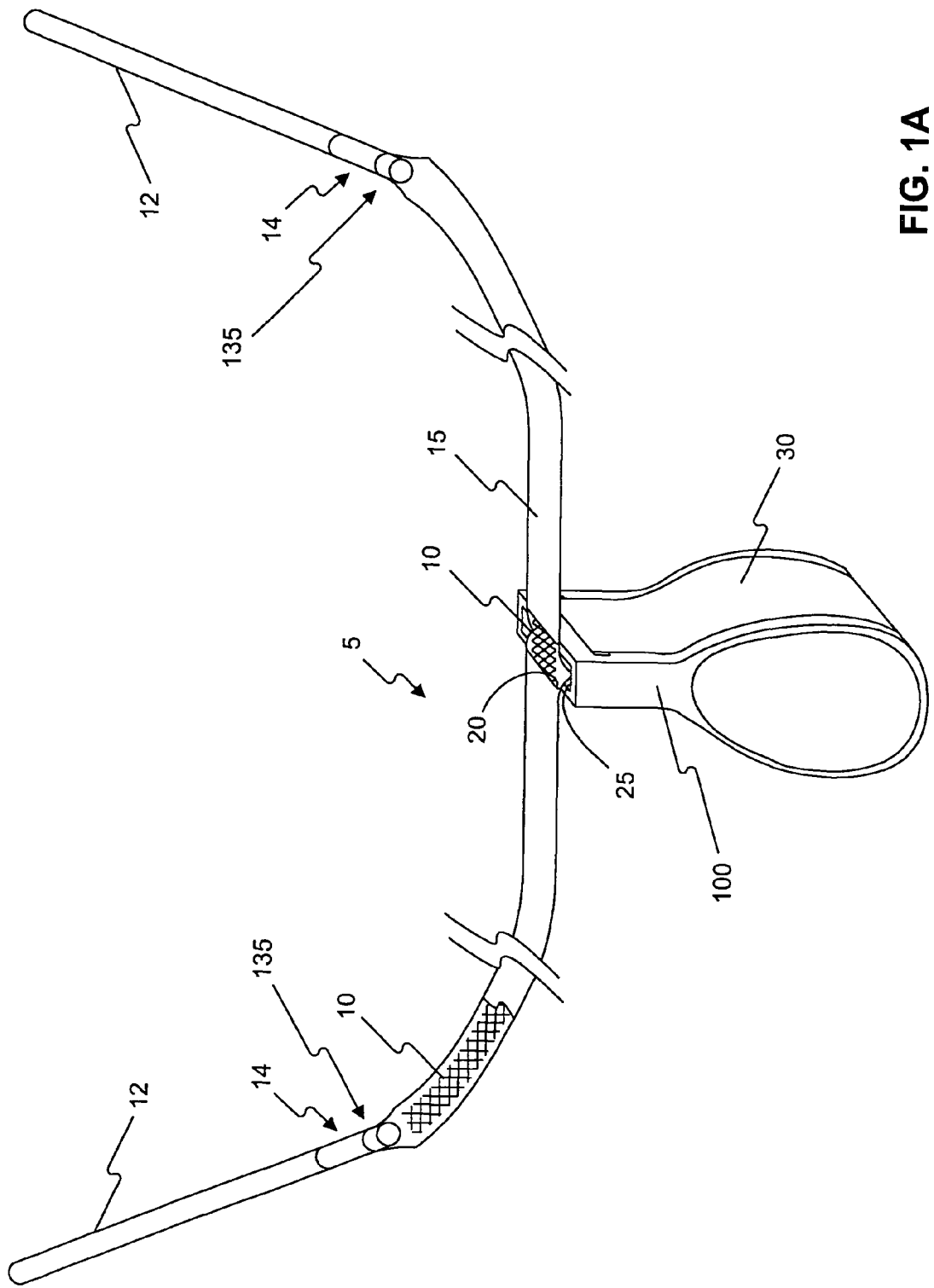

MEDICAL DEVICE POSITIONING ASSEMBLIES AND METHODS

FIELD OF THE INVENTION

This disclosure relates generally to the treatment of stress urinary incontinence ("SUI"), and more particularly, to assemblies and methods for the surgical treatment of SUI in females. The assemblies and methods disclosed herein are additionally useful in a wide variety of other surgical procedures.

BACKGROUND OF THE INVENTION

SUI is the sudden involuntary loss of urine that occurs due to a rise in intra-abdominal pressure. Those who suffer from SUI commonly experience such urine loss during a variety of heightened-stress activities such as laughing, sneezing, or common exercise.

When supported by healthy pelvic floor muscles and strong connective tissue, the urethra is able to maintain a fluid seal and, thus, prevent the involuntary loss of urine during physical stress. When a patient suffers from SUI, weakened pelvic muscle and connective tissue are unable to support the urethra in its natural position. These muscles and tissues are commonly weakened as a result of activities such as vaginal childbirth, and their degradation may be exacerbated by the estrogen loss that accompanies menopause. As a result, as pressure is exerted on the bladder, the urethra cannot remain closed and urine may escape.

Conventional treatments for SUI include the use of diapers, pelvic muscle exercises, biofeedback, medication, and hormone therapy. A wide variety of surgical operations may also be used to correct this condition. Such operations generally involve elevating the bladder neck anteriorly and often include elongating, narrowing, and/or supporting the proximal portion of the urethra.

One type of surgical operation used to correct SUI is the transvaginal tape ("TVT") procedure. The TVT procedure uses a medical device, such as a length of tape or mesh, to reinforce and support the urethra. In such a procedure, the mesh may be surgically implanted in the body of the patient and may be positioned so as to provide support to the urethra when needed, such as in situations of stress. The mesh may be inserted through a small incision in the vagina. The mesh may then be fed distally through the patient's pelvic tissue and positioned beneath the urethra.

Depending on the condition of the patient, it may be desirable to round or dull the edges of a portion of the mesh. Dulling the edges of the mesh may minimize irritation to the urethra after the mesh has been implanted within the body of the patient and may minimize the erosion of urethra cells caused by movement of the mesh relative to the urethra. Existing devices, however, may not enable a physician to locate or position the dulled portion of a mesh while surgically implanting the mesh within the body of the patient.

As shown in FIG. 13, Boston Scientific Corporation's Advantage™ Mid-Urethral Sling System consists of a mesh 10 disposed within sleeve 15. This system includes a centering tab 500 to locate the dulled portion 45 of the mesh 10 while the mesh 10 is disposed within the sleeve 15, and controllably position the dulled portion 45 of the mesh 10 relative to the urethra when implanting the mesh 10 within the body of the patient. The centering tab 500 has a channel 25 that accepts a portion of the sleeve 15 proximate the dulled portion of the mesh 10. The sleeve 15 is fixed to the centering tab 500 through a heat seal at an end of the tab 500. The centering tab 500 includes a through hole 50 next to the seal. The portion of the sleeve 15 disposed within the channel 25 may be visible through the through hole 50.

As FIG. 14 illustrates, once the mesh 10 has been positioned within the patient, the centering tab 500 and the sleeve 15 may be cut into two pieces to assist in removing the assembly 6 (other than the mesh 10) from the body of the patient. Since the sleeve 15 is coupled to the centering tab 500 proximal the through hole 50, the through hole 50 may be useful in determining an appropriate location to sever the centering tab 500. For example, severing the centering tab 500 along the through hole 50 will sever the sleeve 15 and enable the physician to remove the assembly 6 (other than the mesh 10) from the patient's body.

Cutting the centering tab 500 into two pieces, however, results in an additional, small assembly piece 8 that must be removed from the body of the patient. In addition, the small pieces of centering tab 500 may be more difficult to grasp and/or remove from the patient's body after being severed.

The present disclosure provides assemblies for positioning medical devices that avoid some of the aforementioned shortcomings of existing assemblies.

SUMMARY OF THE INVENTION

In accordance with one aspect of the present disclosure, an assembly for positioning a medical device includes a sleeve having a lumen configured to accept a medical device, and a tab. The tab includes a distal portion and a proximal portion. The distal portion is configured to receive the sleeve for positioning the sleeve proximate the proximal portion. The proximal portion is configured such that severing the tab along the proximal portion maintains the tab in one piece.

In embodiments of the present disclosure, the sleeve is positioned relative to the proximal portion so that severing the tab severs the sleeve. A portion of the sleeve has a single layer without a lumen. The medical device is a mesh. The mesh is configured to remain substantially stationary relative to the sleeve. A center portion of the mesh is positioned proximate the tab. The center portion of the mesh includes substantially atraumatic edges.

In some embodiments, the tab is configured to assist in positioning the mesh within the body of a patient. Positioning the sleeve causes a corresponding positioning of the mesh. In further embodiments, the sleeve extends along an outer surface of the proximal portion.

In still further embodiments, the distal portion of the tab defines a channel configured to receive the sleeve. In such embodiments, the sleeve extends from the channel through a first orifice of the tab. The sleeve also extends from the channel through a second orifice of the tab. The channel includes an opening at a distal end of the tab. The opening at the distal end of the tab receives the sleeve.

In additional embodiments of the present disclosure, the tab includes a protrusion on the distal portion of the tab and configured to assist in positioning the tab.

In some embodiments, severing the tab along a length of the proximal portion severs the sleeve. In such embodiments, severing the tab along a length of the tab severs the single layer of the sleeve.

In further embodiments, the tab is formed by a molding process. Alternatively, the tab may be formed by removing a portion of an elongate member. In still further embodiments, the proximal portion has a substantially cylindrical shape. The sleeve is connected to the tab at the distal portion.

In accordance with another aspect of the present disclosure, a tab configured to assist in positioning a medical device includes a distal portion defining a channel configured to receive a sleeve holding the medical device. The tab also includes a substantially cylindrical proximal portion adjacent to the distal portion and configured such that severing the proximal portion along a length maintains the tab in one piece. In some embodiments, the tab defines a first orifice and a second orifice, each in communication with the channel. The first and second orifices are configured to accept the sleeve. The medical device is a mesh.

In some embodiments, the proximal portion is configured to assist in positioning the mesh proximate a urethra of a patient. The proximal portion has a substantially cylindrical shape. The channel includes an opening at a distal end of the tab. The tab is formed by a molding process. The distal portion includes a protrusion configured to assist in manipulating the tab.

In accordance with another aspect of the present disclosure, a method of implanting a medical device to support a urethra of a body includes providing the medical device within a lumen of a sleeve, providing a tab receiving the sleeve, positioning the sleeve and the medical device beneath the urethra, and positioning a portion of the mesh beneath the urethra using the tab. The method also includes severing the tab and the sleeve while maintaining the tab in one piece and removing the tab and the sleeve from the body.

In embodiments, severing the tab includes cutting the tab along a length of the tab. Severing the tab assists in the removal of the tab and the sleeve and includes severing a proximal portion of the tab. In such embodiments, the sleeve extends along an outer surface of the proximal portion and the proximal portion has a substantially cylindrical shape.

In further embodiments of the method, removing the tab and the sleeve includes manipulating the in a first direction and manipulating the sleeve in a second direction substantially opposite the first direction. The medical device is a mesh.

In other embodiments, a distal portion of the tab defines a channel configured to receive the sleeve. In such embodiments, the sleeve extends from the channel through a first orifice of the tab. The sleeve extends from the channel through a second orifice of the tab. The channel includes an opening at a distal end of the tab.

Both the foregoing general description and the following detailed description are exemplary and explanatory only, and are not restrictive of the invention as claimed.

BRIEF DESCRIPTION OF THE DRAWINGS

Exemplary embodiments of the present disclosure are illustrated in the accompanying drawings. Wherever possible, the same reference numbers will be used throughout the drawings to refer to the same or like parts. The drawings are not necessarily to scale. Emphasis is instead generally being placed upon illustrating the principles of the present disclosure.

FIG. 1A is a medical device and its positioning assembly according to an embodiment of the present disclosure.

DETAILED DESCRIPTION

Figure 1B:
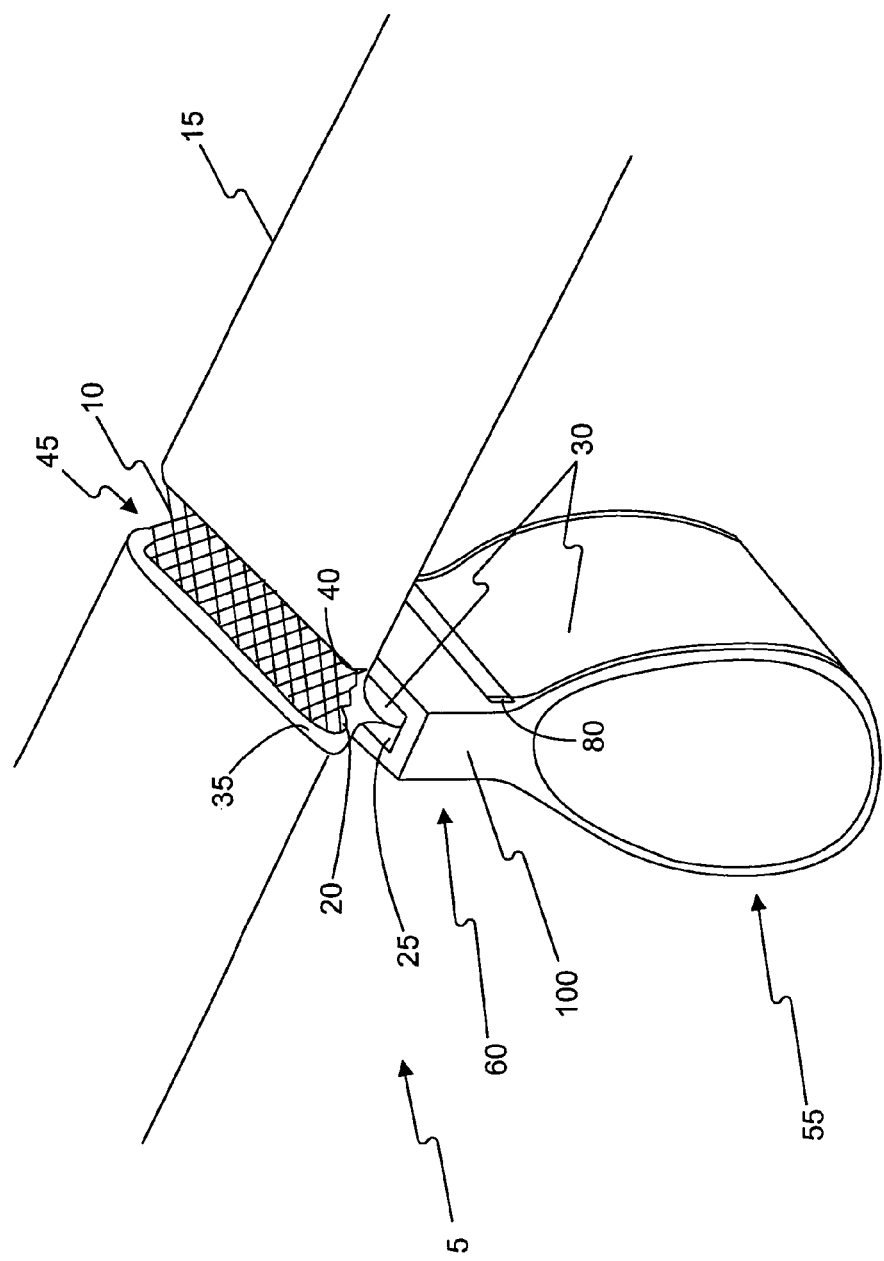
FIG. 1B is an enlarged elevation view of a portion of the medical device and positioning assembly of FIG. 1A, according to an embodiment of the present disclosure.

As shown in FIG. 1A, in one embodiment of the present disclosure a medical device positioning assembly 5 may include a sleeve 15 defining a lumen 20, a centering tab 100, and a tube 12 connected to each distal end 135 of the sleeve 15. The tubes 12 may be hollow or solid, and may be any substantially atraumatic shape useful for manipulating the tubes 12 within the body of a patient. For example, the tubes 12 may have a cylindrical or ovular cross-section, and may be substantially rigid. Additionally, the tubes 12 may have any length and/or diameter useful for assisting in positioning a medical device within the body.

The tubes 12 may be made from any metal, plastic, alloy, or polymer known in the art, and may be comprised of a substantially biocompatible, bioabsorbable and/or biodegradable material. In some embodiments, the tubes 12 may be made from the same material as the sleeve 15. In such embodiments, the distal ends 135 of the sleeve 15 may be, for example, heat-sealed to the proximal ends 14 of the tubes 12. In other embodiments, the distal ends 135 of the sleeve 15 may be connected to the proximal ends 14 of the tubes 12 by any other conventional means such as, for example, shrink wraps or adhesives. The tubes 12 may be configured such that manipulating at least one of the tubes 12 may cause a corresponding movement in at least the distal end 135 of the sleeve 15 connected thereto.

FIG. 1B illustrates a portion of the medical device positioning assembly 5 of FIG. 1A. Aspects of the assembly 5 may be used, for example, to assist in positioning a medical device, such as a mesh 10, within the body of a patient. As will be described in greater detail below, the mesh 10 may be implanted proximate the urethra to treat SUI in female patients. As shown in FIG. 1B, the sleeve 15 of assembly 5 may define a lumen 20, and at least a portion of the mesh 10 may be disposed within the lumen 20 of the sleeve 15. The mesh 10 may be free-floating within the sleeve 15. Alternatively, the mesh 10 may be fixed to the sleeve 15.

The mesh 10 may be made from any biocompatible material known in the art. Such materials may include, for example, polyethylene, polytetrafluoroethylene ("PTFE"), or expanded polytetrafluoroethylene ("EPTFE"). The mesh 10 may comprise any shape, size, design, or configuration known in the art. Such configurations may be useful in treating SUI. For example, as shown in FIG. 2B, the mesh 10 may comprise a crisscrossed or chain link fence-like design. In such configurations, the fibers or strands of the mesh 10 may be woven, linked, or otherwise connected together, and may share the stress of a supported load. Alternatively, the mesh 10 may be a substantially uniform piece of material (not shown) or may have a woven pattern (not shown) similar to a woven blanket.

As illustrated in FIG. 2B, a center portion 45 of the mesh 10 may include edges 47 that are dulled, rounded, and/or substantially atraumatic. In some embodiments, the center portion 45 of the mesh 10 may be approximately four centimeters long and may be located proximate the centering tab 100. As will be described in greater detail below, the center portion 45 of the mesh 10 may also be located proximate an opening or removed section in the sleeve 15. The atraumatic edges 47 of the center portion 45 may be useful, for example, in minimizing irritation to the urethra. The atraumatic edges 47 of the center portion 45 may also be useful in minimizing the gradual erosion of urethra cells caused by movement of the mesh 10 relative to the urethra of the patient after the mesh 10 has been surgically implanted. Such movement may occur due to ordinary physical activity.

The sleeve 15 of the medical device positioning assembly 5 may be comprised of any biocompatible material known in the art. Such materials may include, for example, polyethylene, PTFE, and EPTFE, and may be opaque, semi-opaque, or transparent. The sleeve 15 may be comprised of one material or, in some embodiments, the sleeve 15 may be a multilayered sleeve comprised of one or more of the materials already mentioned. The sleeve 15 may be any length or width useful for implanting and positioning the mesh 10 within the body of the patient, and may be flexible and easily manipulable when the mesh 10 is disposed therein. In some embodiments, the sleeve 15 may be approximately three feet long and approximately one half inch wide, and the dimensions of the sleeve 15 may be determined by the length and/or width of the mesh 10. For example, in each of the embodiments described herein, the sleeve 15 may be long enough and wide enough to define a lumen 20 that is appropriately sized for accepting the mesh 10.

Figure 2A:
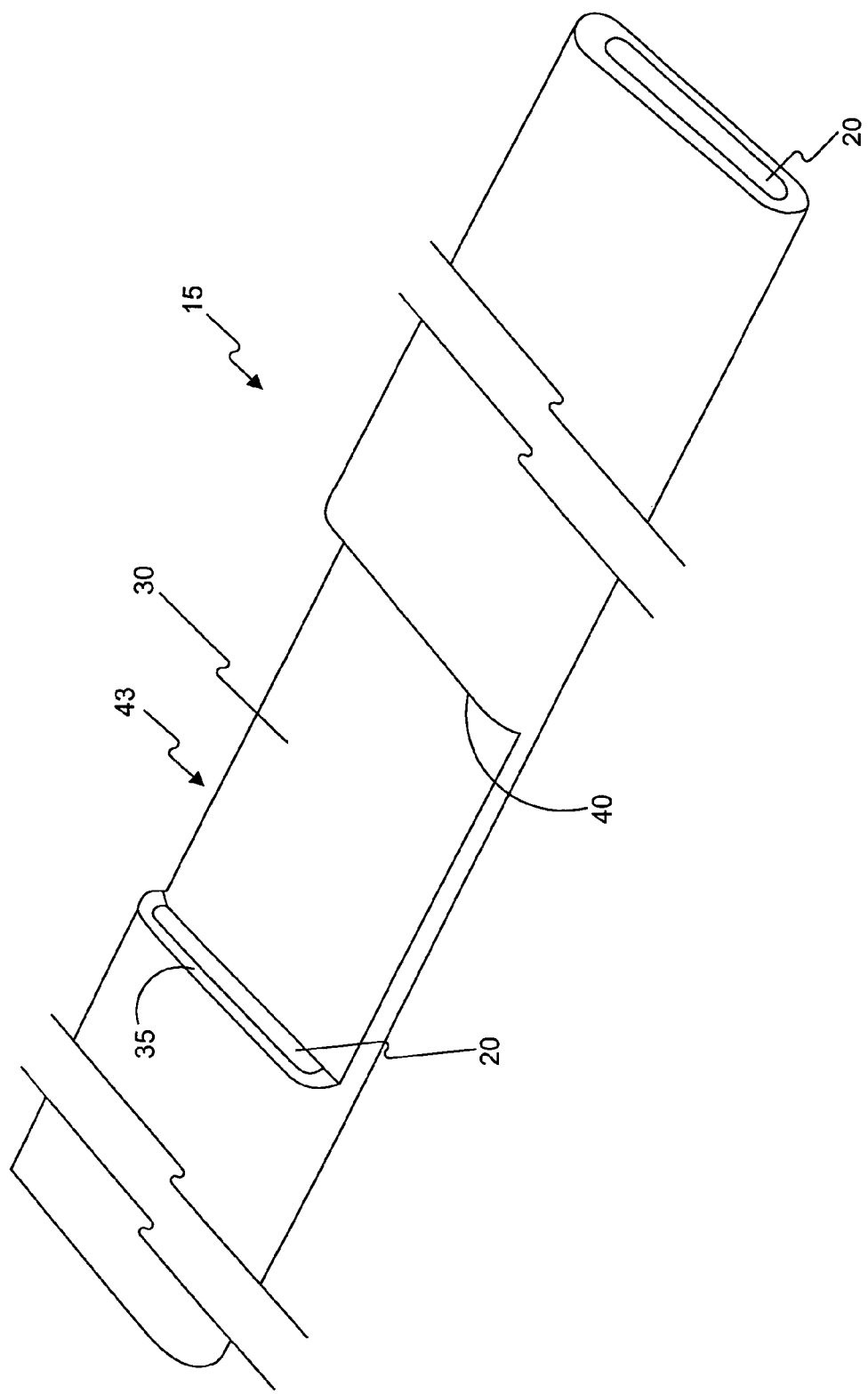
FIG. 2A is an elevation view of a sleeve of the medical device positioning assembly of FIG. 1A.
Figure 2B:
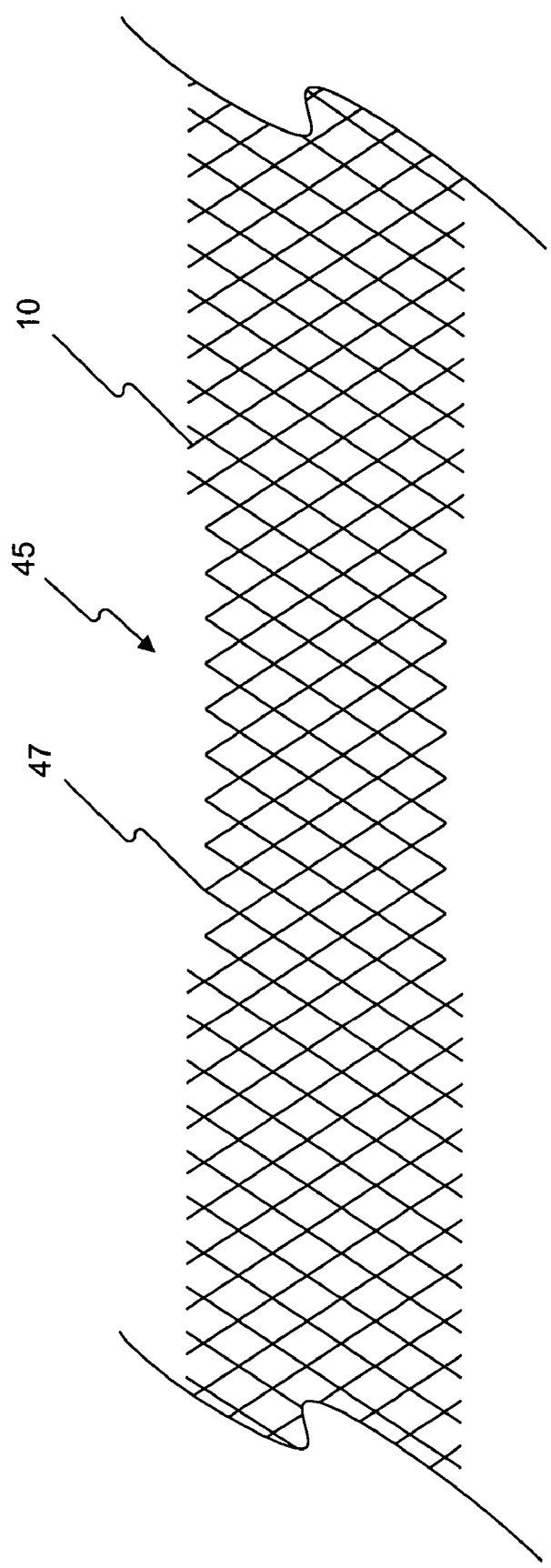
FIG. 2B is a plan view of a portion of the mesh of FIG. 1A.

As illustrated in FIG. 2A, in some embodiments of the present disclosure, a portion of the sleeve 15 may be removed so as to define a single layer 30. The single layer 30 may be located proximate a center section 43 of the sleeve 15. Alternatively, the single layer 30 may be located anywhere along the sleeve 15 to assist in locating and/or positioning a desired portion of the mesh 10.

As shown in FIG. 1B, a portion of the single layer 30 of the sleeve 15 may be disposed within a channel 25 of the centering tab 100. As will be described in greater detail below, in such embodiments, the single layer 30 of the sleeve 15 may extend through the channel 25, through orifices 80, 85 on the sides of the centering tab 100, and along or around a proximal portion 55 of the centering tab 100.

As shown in FIGS. 1B and 2A, removing a portion of the sleeve 15 may define a first surface 35 and a second surface 40 of the sleeve 15. The first surface 35 and the second surface 40 may be located opposite one another when the portion of the sleeve 15 is removed. When the mesh 10 is disposed within the lumen 20 of the sleeve 15, and a portion of the sleeve 15 has been removed to define a single layer 30, a center portion 45 of the mesh 10 may be at least partially exposed, as shown in FIG. 1B. Moreover, when the center section 43 (FIG. 2A) of the sleeve 15 is disposed within the channel 25 of the centering tab 100, the first surface 35 may be drawn proximate the second surface 40 so as to expose as little of the center portion 45 of the mesh 10 as possible. Thus, the first and second surfaces 35, 40 of the sleeve 15 may be configured to abut or mate proximate the center portion 45 of the mesh 10 when the mesh 10 is disposed within the lumen 20 of the sleeve 15 and the single layer 30 of the sleeve 15 is disposed within the channel 25 and around the proximal portion 55 of the centering tab 100.

When the mesh 10 is disposed within the lumen 20 of the sleeve 15, and the centering tab 100 is engaged with or operably connected to the sleeve 15, the mesh 10 may be configured to remain approximately stationary relative to the sleeve 15 and the centering tab 100. In such embodiments, the mesh 10 may be unattached to, or free-floating within, the lumen 20 of the sleeve 15, and the center portion 45 of the mesh 10 may be located proximate the centering tab 100. Thus, the centering tab 100 may be configured to assist in positioning the sleeve 15 within the body of a patient, and positioning the sleeve 15 may cause a corresponding positioning of the center portion 45 of the mesh 10.

Figure 3:
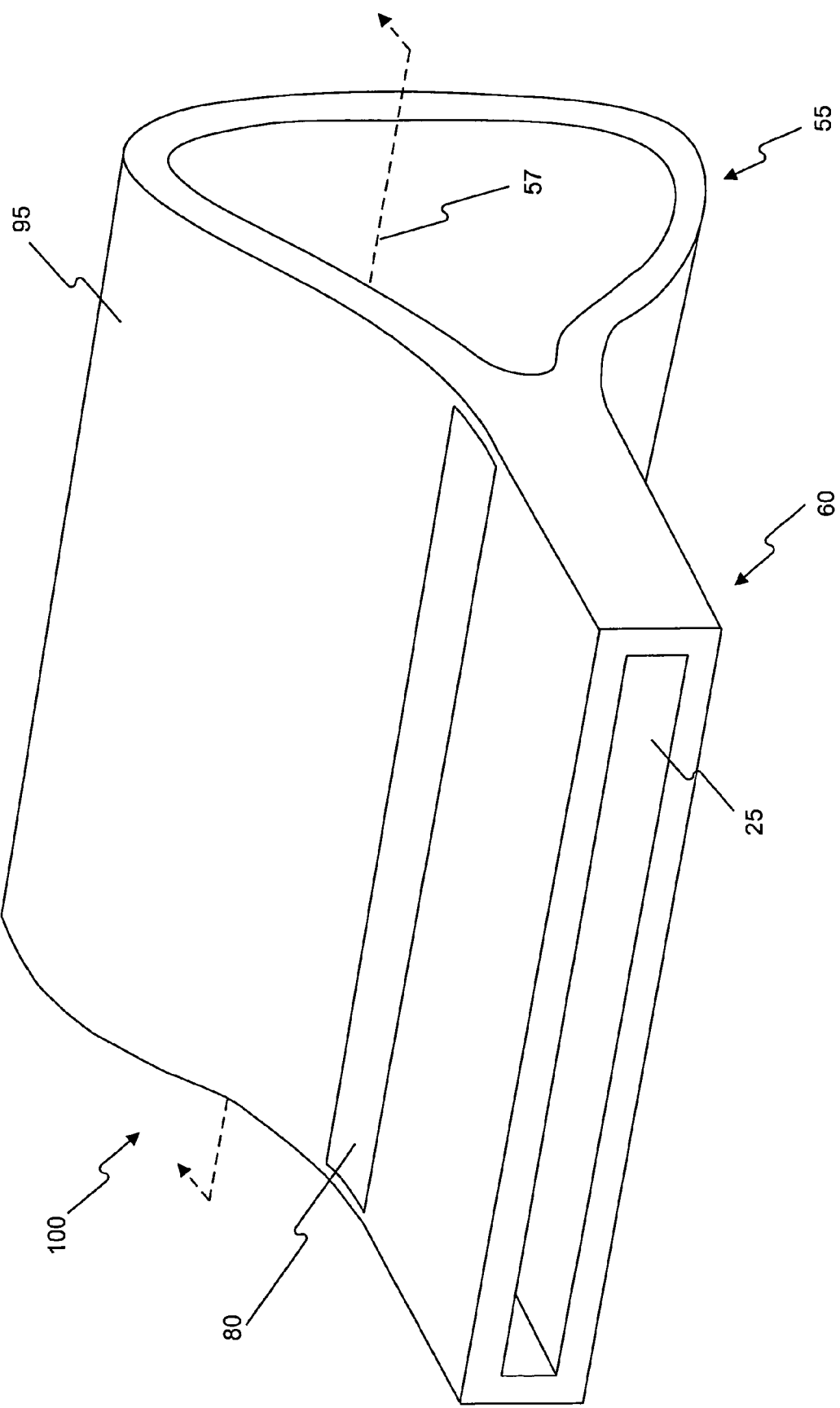
FIG. 3 is an elevation view of the centering tab of FIG. 1A.

The centering tab 100 may be made of any material known in the art, such as, for example, polyethylene, PTFE, or EPTFE, and may be of any color, such as blue, to assist the user in viewing the centering tab 100. The centering tab 100 may be sized and otherwise configured to assist in positioning a portion of the mesh 10 and/or the sleeve 15 within the body of a patient. As shown in FIG. 3, a centering tab 100 of the present disclosure may further include a distal portion 60 and a proximal portion 55. The distal portion 60 of the centering tab 100 may be flat relative to the proximal portion 55 of the centering tab 100. The distal portion 60 may define at least one channel 25 of the centering tab 100 and, as further illustrated in FIG. 4, in some embodiments the channel 25 may extend through the entire length of the distal portion 60. The proximal portion 55 of the centering tab 100 may be rounded, semicircular, ovular, teardrop-shaped, or any other shape useful in manipulating the centering tab 100 with respect to the patient. The proximal portion 55 of the centering tabs disclosed herein may be substantially cylindrical or tube-like. The configuration of the proximal portion 55 may facilitate severing the centering tab 100 such that a one-piece construction is maintained after the proximal portion 55 has been severed. At least a portion of the assembly 5 and mesh 10 may be positioned through lateral, distal, proximal, or other manipulations of the centering tabs described herein.

Figure 4:
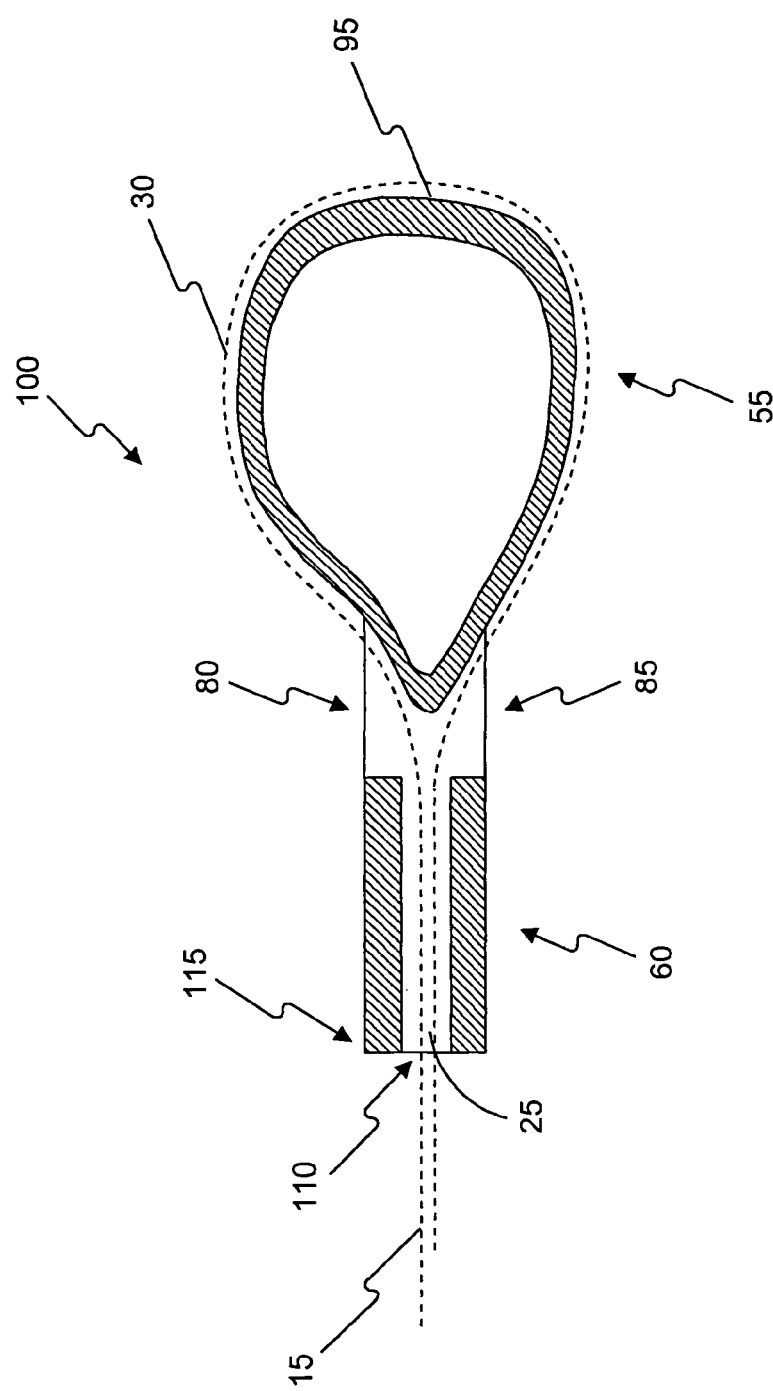
FIG. 4 is a side cross-sectional view of the centering tab of FIG. 3.

The proximal portion 55 may include an outer surface 95 for accepting at least a portion of the sleeve 15. As shown in FIG. 4, the centering tab 100 may further include a first orifice 80 and a second orifice 85. The first and second orifices 80, 85 of the centering tab 100 may be located between the distal portion 60 and the proximal portion 55 of the centering tab 100 and, in some embodiments of the present disclosure, the channel 25 of the centering tab 100 may be in communication with at least one of the orifices 80, 85. In other embodiments of the present disclosure, the centering tab 100 may include more than one channel 25. In such embodiments, at least one channel 25 may communicate with the first orifice 80 and at least one other channel 25 may communicate with the second orifice 85. The centering tab 100 may further include at least one opening 110 at a distal end 115.

As illustrated by the dotted line 15, 30 of FIG. 4, in some embodiments at least a portion of the sleeve 15 may be fed through opening 110, through channel 25, out of first orifice 80, around and in communication with outer surface 95, into second orifice 85, and out of channel 25 through opening 110.

In such embodiments, the single layer 30 of the sleeve 15 may extend around and along the outer surface 95 of the proximal portion 55. Thus, severing the centering tab 100 along a longitudinal axis 57 (FIG. 3) of the proximal portion 55 may assist in removing the sleeve 15 from the body of the patient while maintaining a one-piece centering tab 100.

Figure 5:
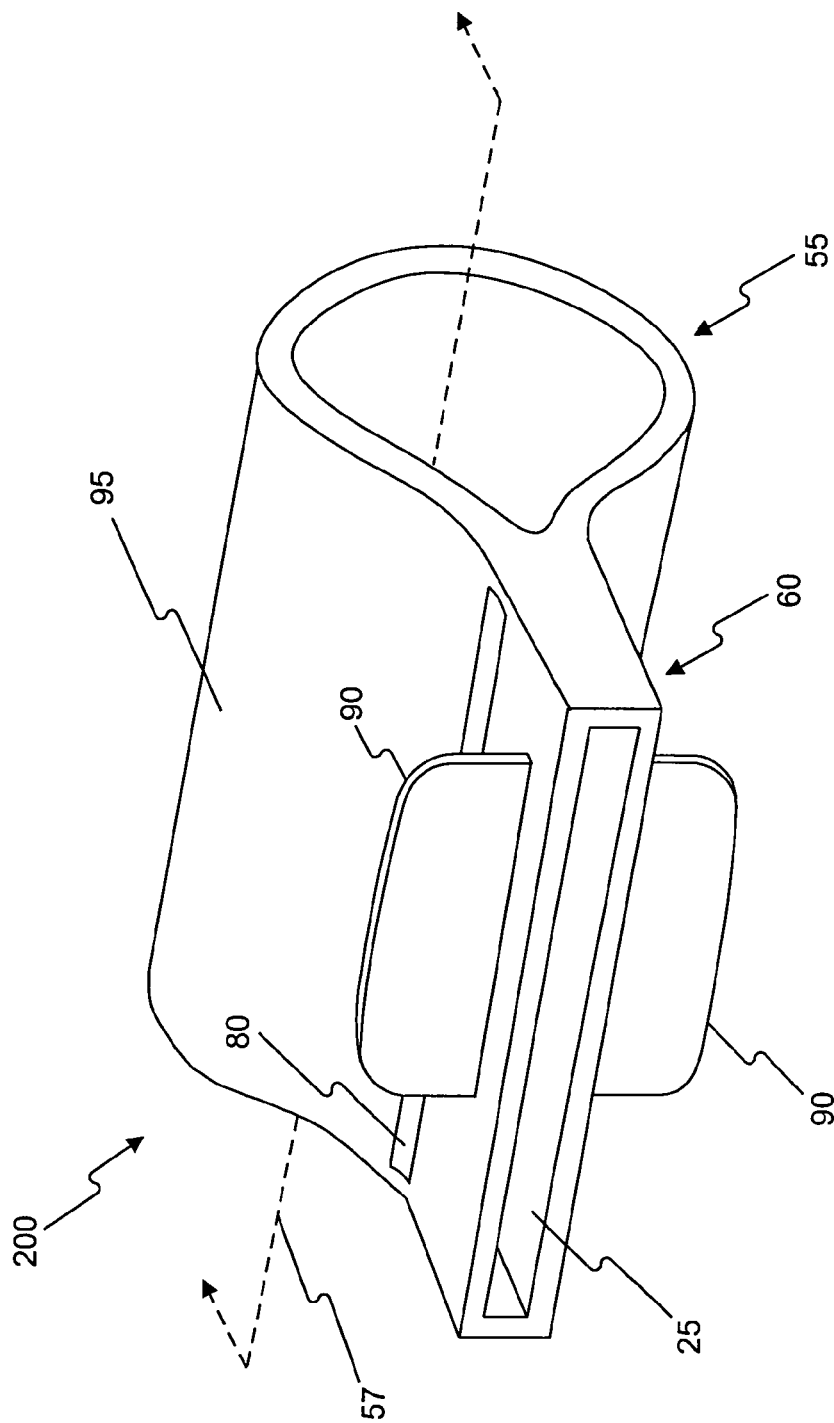
FIG. 5 is an elevation view of a centering tab according to a further embodiment of the present disclosure.

As shown in FIG. 5, in another embodiment of the present disclosure the centering tab 200 may further include at least one protrusion 90. The protrusion 90 may be positioned in any location on the centering tab 200 useful in manipulating the centering tab 200 with respect to the body of the patient. The protrusions 90 may be any shape known in the art. For example, in some embodiments, the protrusions 90 may be flat, substantially rectangular tabs. The protrusions 90 may extend approximately perpendicular from the distal portion 60 of the centering tab 200. The protrusions 90 may be attached to the centering tab 200 through any conventional means known in the art. In some embodiments, the protrusions 90 may be formed from the same material as the centering tab 200. In embodiments where the centering tab 200 is created through a molding process, the protrusions 90 may be molded to the distal portion 60 of the centering tab 200.

Figure 6:
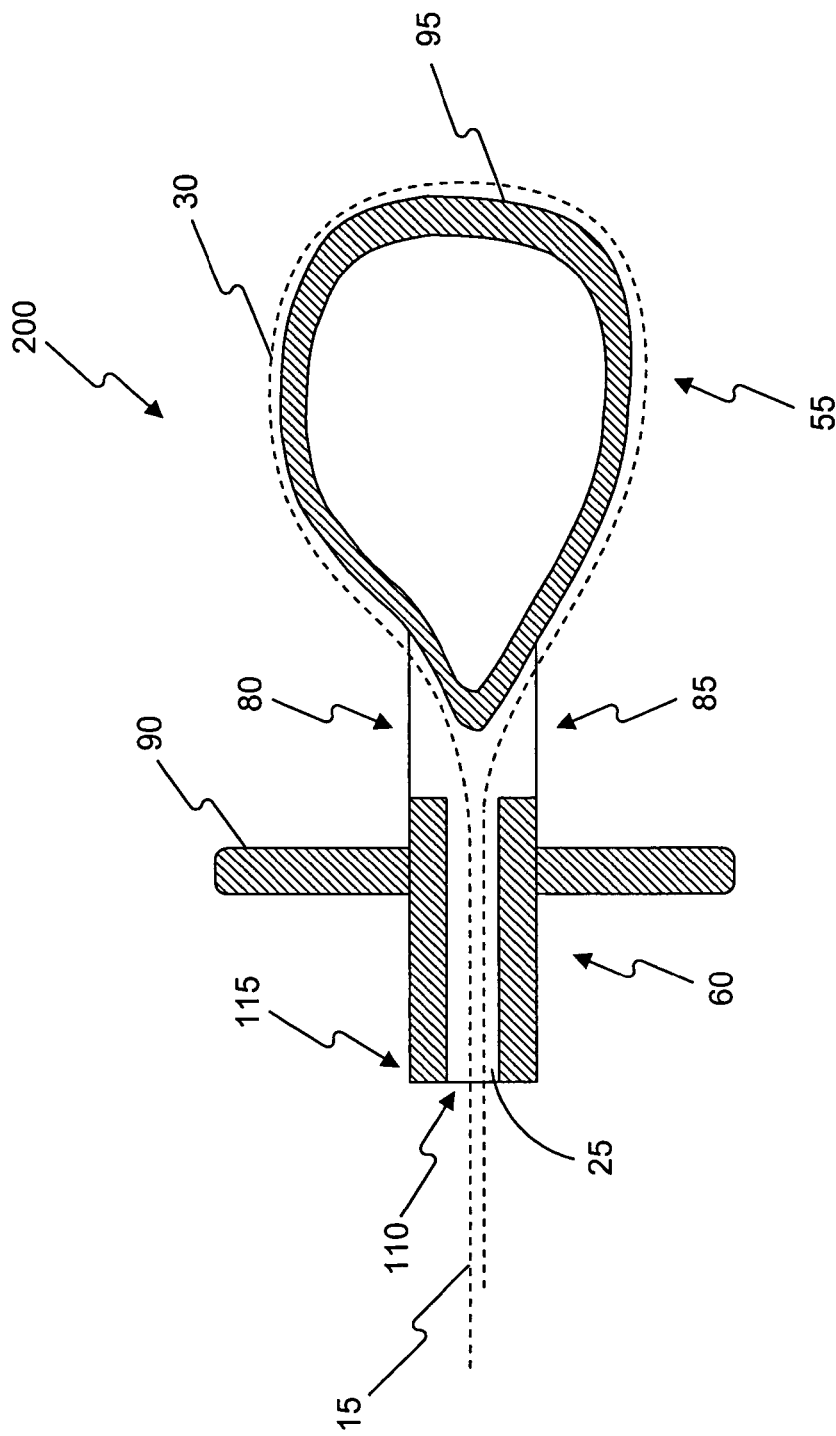
FIG. 6 is a side cross-sectional view of the centering tab of FIG. 5.

As FIG. 6 illustrates, the protrusions 90 may not extend within the channel 25 of the centering tab 200. Thus, as described with respect to FIG. 4, the sleeve 15 may enter through the opening 110 of the centering tab 200, and may extend through channel 25 and exit first orifice 80. The sleeve 15 may extend around and along the outer surface 95 of the proximal portion 55 of the centering tab 200 and may enter the second orifice 85. The sleeve 15 may extend through the channel 25 and may exit opening 110 at the distal end 115 of the centering tab 200. This sleeve path is illustrated by the dotted line 15, 30 of FIG. 6. Thus, severing the centering tab 200 along a longitudinal axis 57 (FIG. 5) of the proximal portion 55 may assist in removing the sleeve 15 from the body of the patient while maintaining a one-piece centering tab 200.

Figure 7:
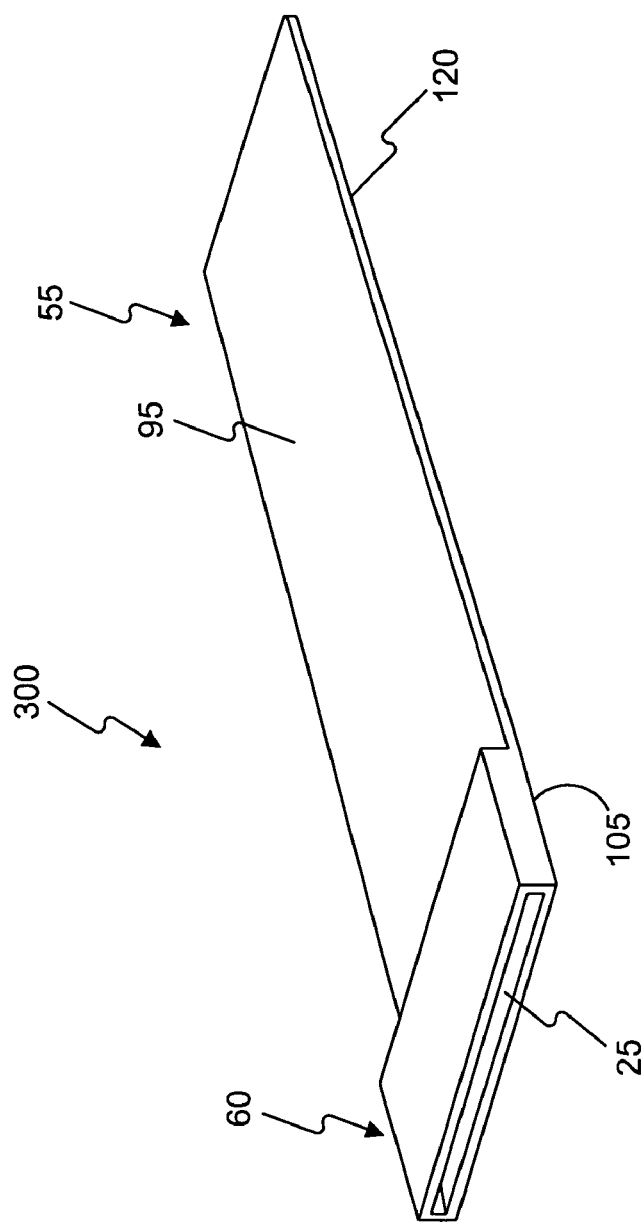
FIG. 7 is an elevation view of an unformed centering tab of an exemplary embodiment of the present disclosure.
Figure 8:
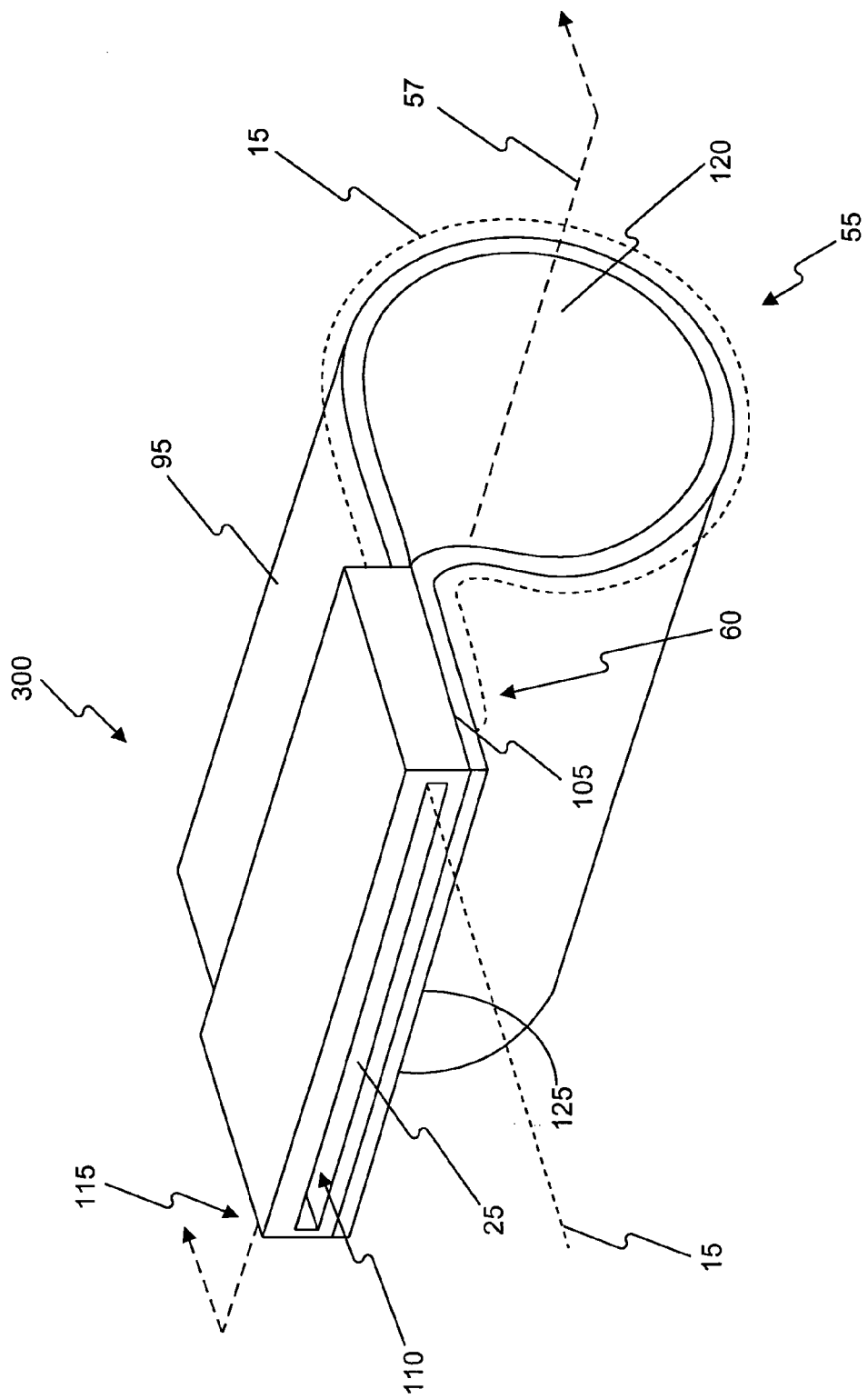
FIG. 8 is an elevation view of a formed centering tab of the embodiment of FIG. 7.

The centering tabs 100, 200 of FIGS. 3-6 may be formed by, for example, a molding process. As illustrated in FIGS. 7 and 8, however, the centering tab 300 may also be formed by removing at least a portion of an elongate member. The elongate member may comprise any structure known in the art such as, for example, a tube, a cannula, a rod, or channel. In any of the embodiments described herein, the elongate member may be hollow so as to define a channel 25 as shown in FIG. 7.

In embodiments such as the embodiments of FIGS. 7 and 8 where a centering tab 300 is formed by removing a portion of an elongate member, the centering tab 300 may include a distal portion 60 and a proximal portion 55. FIG. 7 illustrates an unformed centering tab 300 wherein a portion of an elongate member has been removed to define an outer surface 95, an inner surface 120 of the proximal portion 55, and an undersurface 105 of the distal portion 60.

As illustrated in FIG. 8, to form a centering tab 300 in such an embodiment, the proximal portion 55 may be bent, rolled, or otherwise manipulated to attach to the undersurface 105 of the distal portion 60. A portion of the inner surface 120 of the proximal portion 55 may be connected to the undersurface 105 of the distal portion 60 by any conventional means. For example, in some embodiments the inner surface 120 may be heat-sealed, glued, or otherwise attached to the undersurface 105. In embodiments of the present disclosure where the inner surface 120 is heat-sealed to the undersurface 105 of the centering tab 300, the channel 25 may be shielded from the heat applied to the undersurface 105 such that the channel 25 may remain open once the inner surface 120 is connected to the undersurface 105. The channel 25 may be shielded by any means known in the art. For example, a strip of heat-resistant material may be inserted into the channel 25 while heat is applied.

Thus, in the embodiment illustrated in FIG. 8, a portion of the sleeve 15 may extend through the channel 25 and may extend over and along the outer surface 95 of the proximal portion 55. In such embodiments, the portion of the sleeve 15 extending along the outer surface 95 may extend around substantially the entire circumference and/or length of the proximal portion 55 and may be attached to a connection surface 125 of the distal portion 60. As described above with respect to the connection between the undersurface 105 of the distal portion 60 and the inner surface 120 of the proximal portion 55, a portion of the sleeve 15 may be connected to the connection surface 125 by any conventional means. Such means may include, for example, heat-sealing. In embodiments where the sleeve 15 is connected to the connection surface 125, a portion of the sleeve 15 need not be removed, and a center section 43 of a single layer 30 need not be formed. Instead, the sleeve 15 may include two slits (not shown) configured to accept the mesh 10 such that a portion of the sleeve 15 may extend over and along the outer surface 95 without the mesh 10 being disposed within the portion. In such embodiments, the mesh 10 may exit a first slit (not shown) and enter a second slit (not shown) and the center portion 45 (FIG. 2B) of the mesh 10 may be substantially perpendicular to the centering tab 300.

Moreover, in such embodiments the sleeve 15 may be comprised of the same material as the centering tab 300. For example, wherein the sleeve 15 is heat-sealed to the centering tab 300, both the sleeve 15 and the centering tab may be comprised of the same material to assist in forming a relatively strong connective bond between the sleeve 15 and the centering tab 300. This same material may be, for example, polyethylene or any of the other materials described above.

As described with respect to the embodiments of FIGS. 3-6, the centering tab 300 of FIGS. 7 and 8 may also include an opening 110 at the distal end 115 of the centering tab 300. The sleeve 15 may enter through the opening 110 at the distal end 115 of the centering tab 300, extend around and along the outer surface 95 of the proximal portion 55, and connect to the connection surface 125. This sleeve path is illustrated by the dotted line 15 of FIG. 8. Thus, severing the proximal portion 55 of the centering tab 300 along the longitudinal axis 57 of the proximal portion 55 as illustrated in FIG. 8 (or otherwise along the length of proximal portion 55) may sever both the centering tab 300 and the sleeve 15. Severing the centering tab 300 along the longitudinal axis 57 may assist in removing the sleeve from the body of a patient while maintaining a one-piece centering tab 300.

During use, a medical device such as mesh 10, using a positioning assembly 5 of the present disclosure, may be surgically implanted into the body of a patient. Such a method may be useful in treating, for example, SUI and may include TVT procedures. In a TVT procedure, a medical device, such as the mesh 10 of the present disclosure, may be used to support at least a portion of the urethra of the patient.

Figure 9:
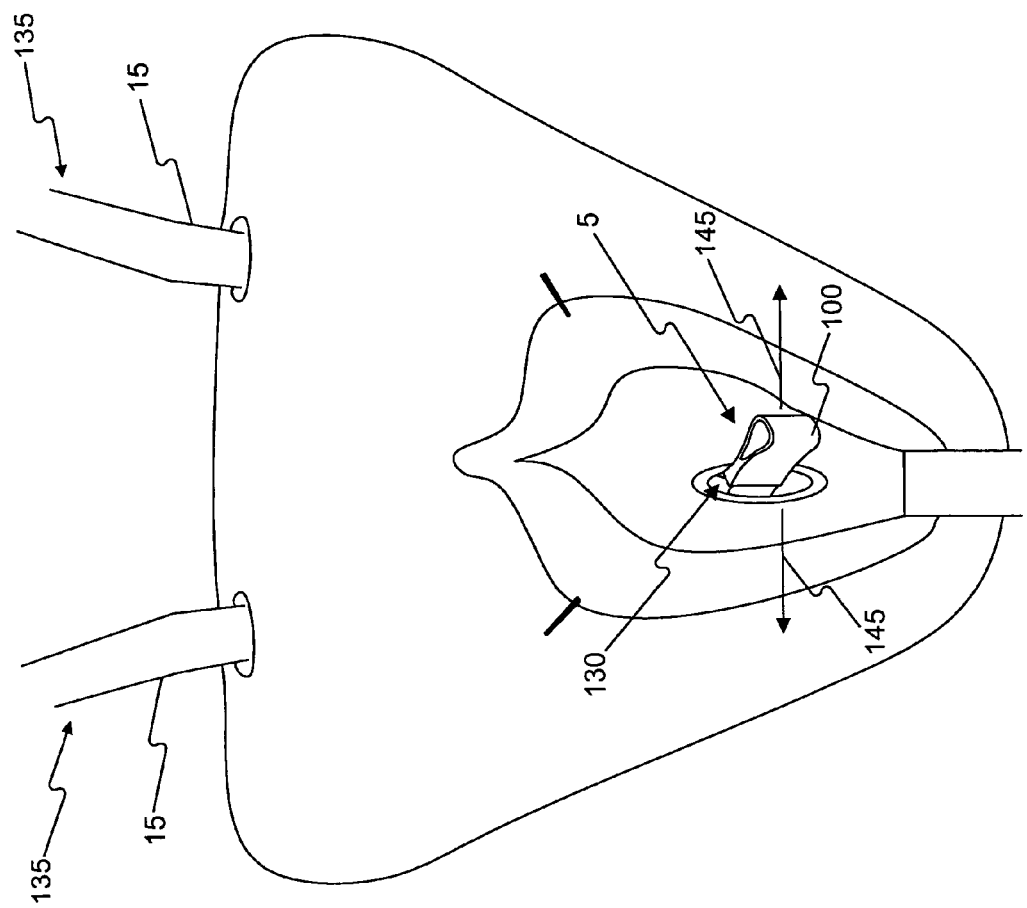
FIG. 9 is a front view of a portion of the medical device positioning assembly of FIG. 1 positioned within the body of a patient.
Figure 10:
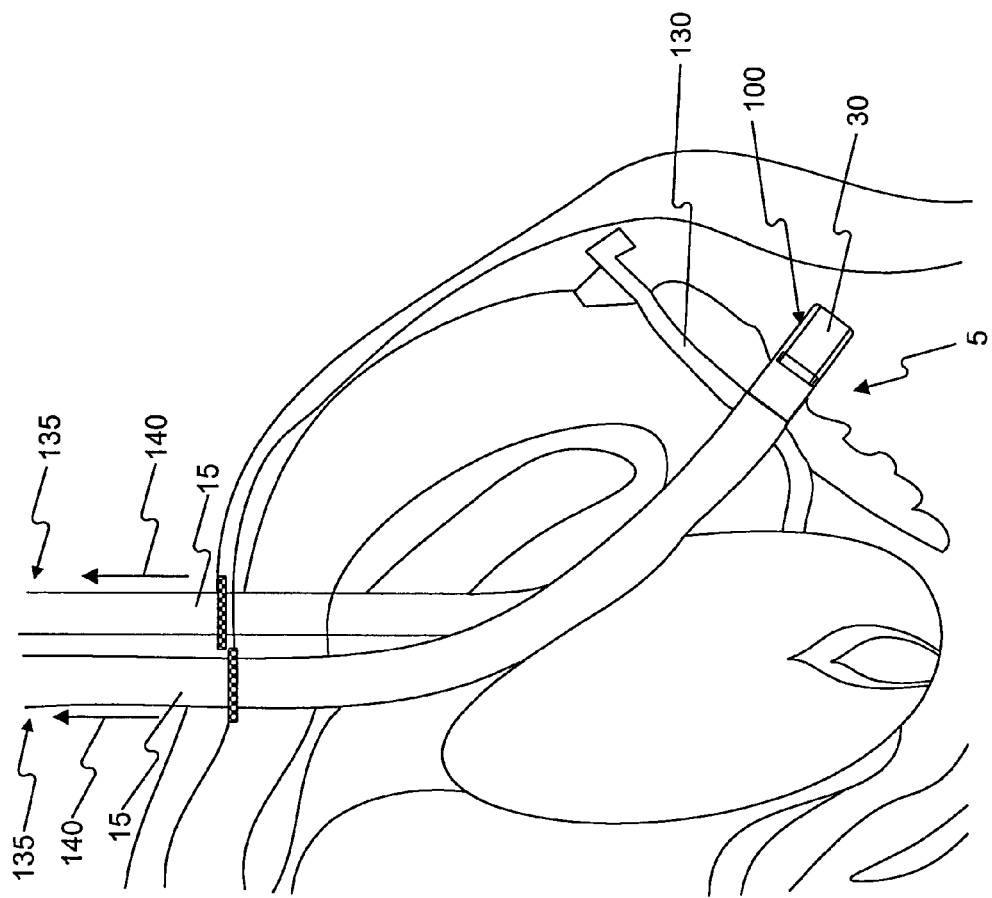
FIG. 10 is a partial cutaway view of the body of a patient having a portion of a medical device positioning assembly of an embodiment of the present disclosure positioned therein.

As illustrated in FIGS. 9 and 10, at least a portion of the sleeve 15 may be positioned in the body of the patient proximate the urethra 130. The mesh 10 (not shown) may be disposed within the lumen 20 (not shown) of the sleeve 15 prior to positioning the sleeve 15. Once the sleeve 15 has been implanted, the distal ends 135 of the sleeve 15 may be pulled distally until the center section 43 (FIG. 2A) of the sleeve 15 and, correspondingly, the center portion 45 (FIGS. 1B and 2B) of the mesh 10 are proximate the urethra 130. Such distal movement is illustrated by arrows 140 in FIG. 10 and may be facilitated by manipulating the tubes 12 (FIG. 1A) distally. The centering tab 100 may then be manipulated, for example, laterally to position the sleeve 15 and the center portion 45 of the mesh 10 beneath and proximate the urethra 130, as illustrated by arrows 145 in FIG. 9. As described above, the location of the centering tab 100 may approximately correspond to the location of the center portion 45 of the mesh 10, and the edges 47 of the center portion 45 of the mesh 10 may be substantially atraumatic so as to reduce damage to the urethra 130 after implantation.

Figure 11:
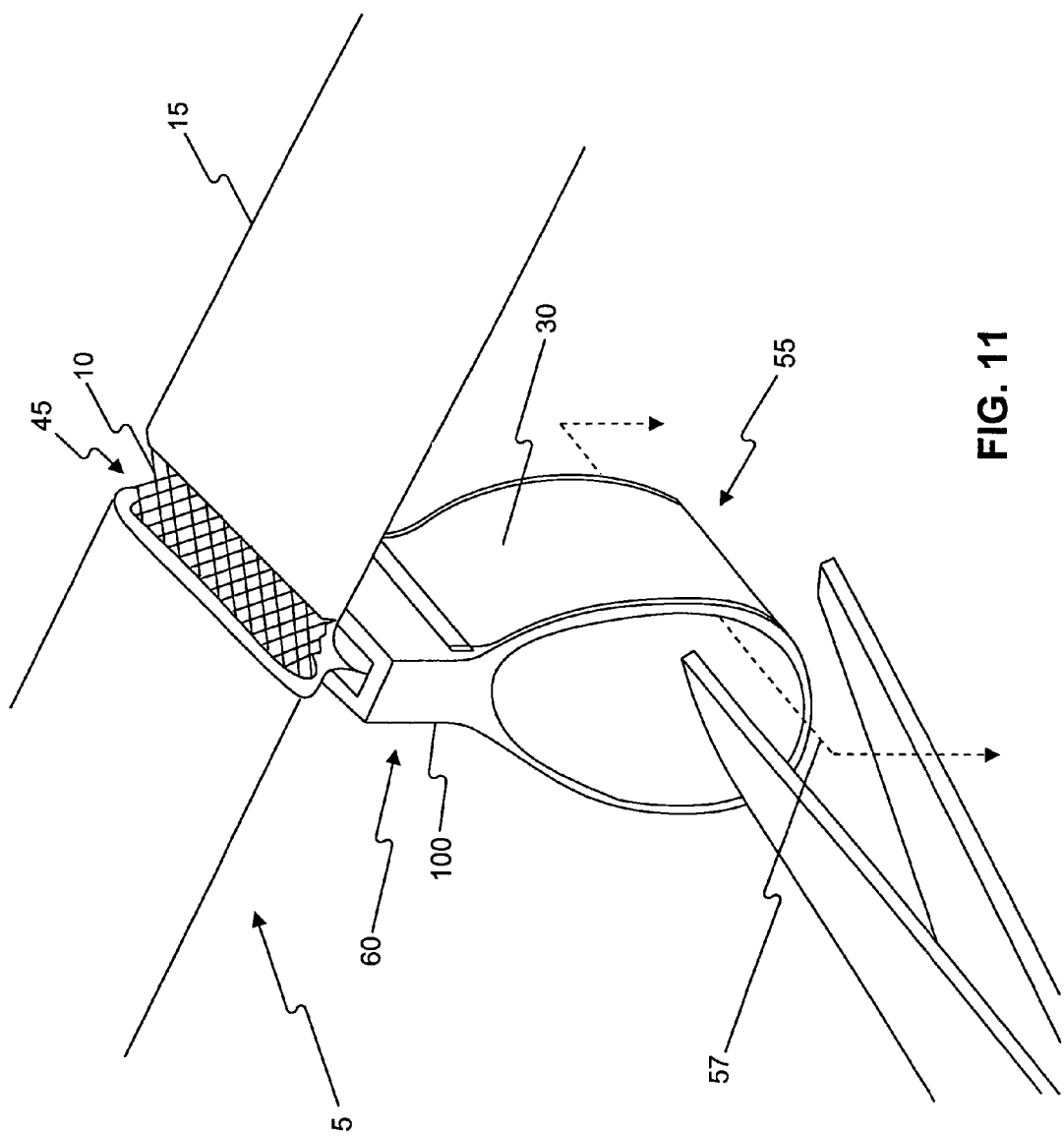
FIG. 11 is a view of the medical device and its positioning assembly of FIG. 1B, showing the severing of the assembly, according to an embodiment of the present disclosure.
Figure 12:
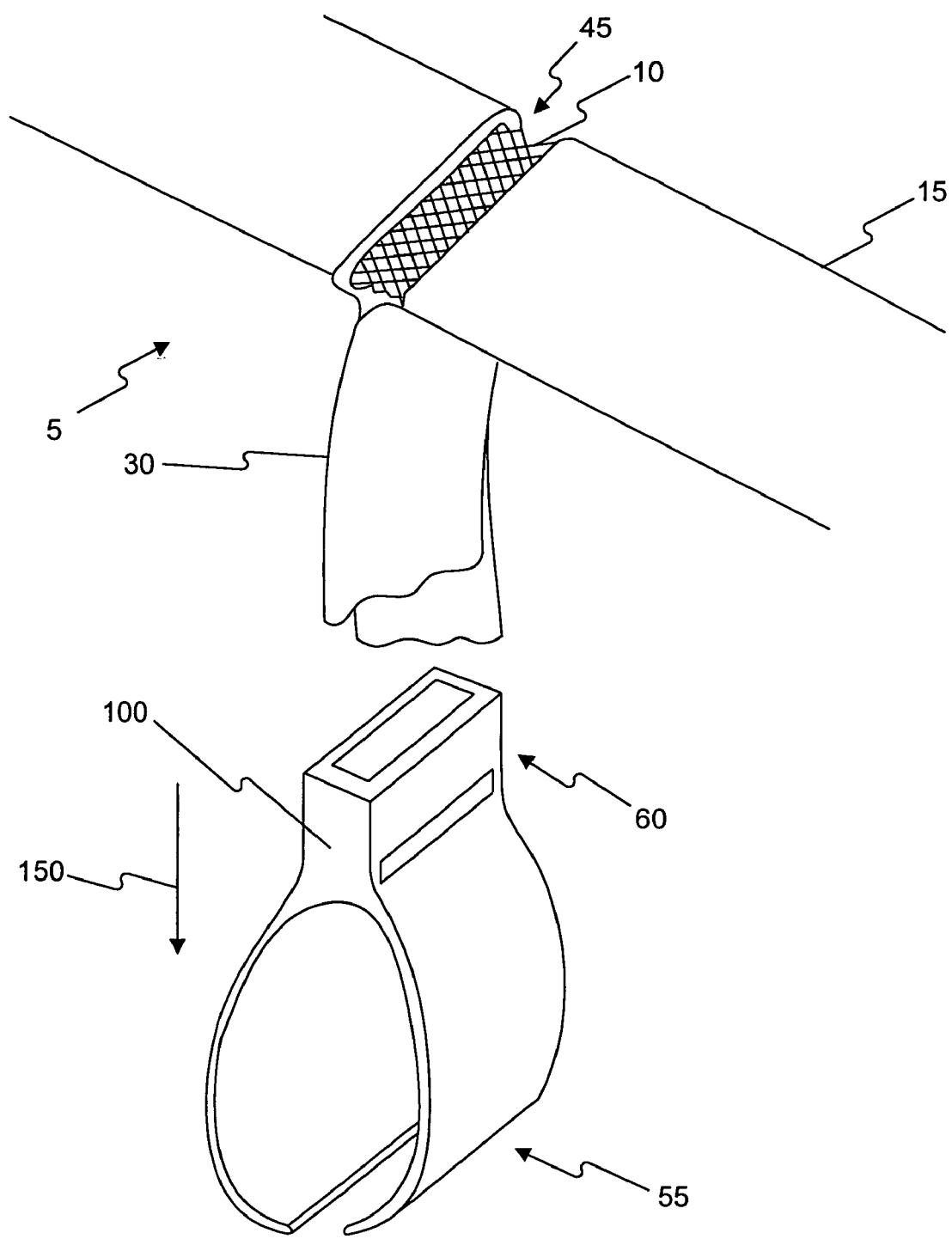
FIG. 12 is a further view of the medical device and its positioning assembly of FIG. 1B, showing the removal of the centering tab.
Figure 13:
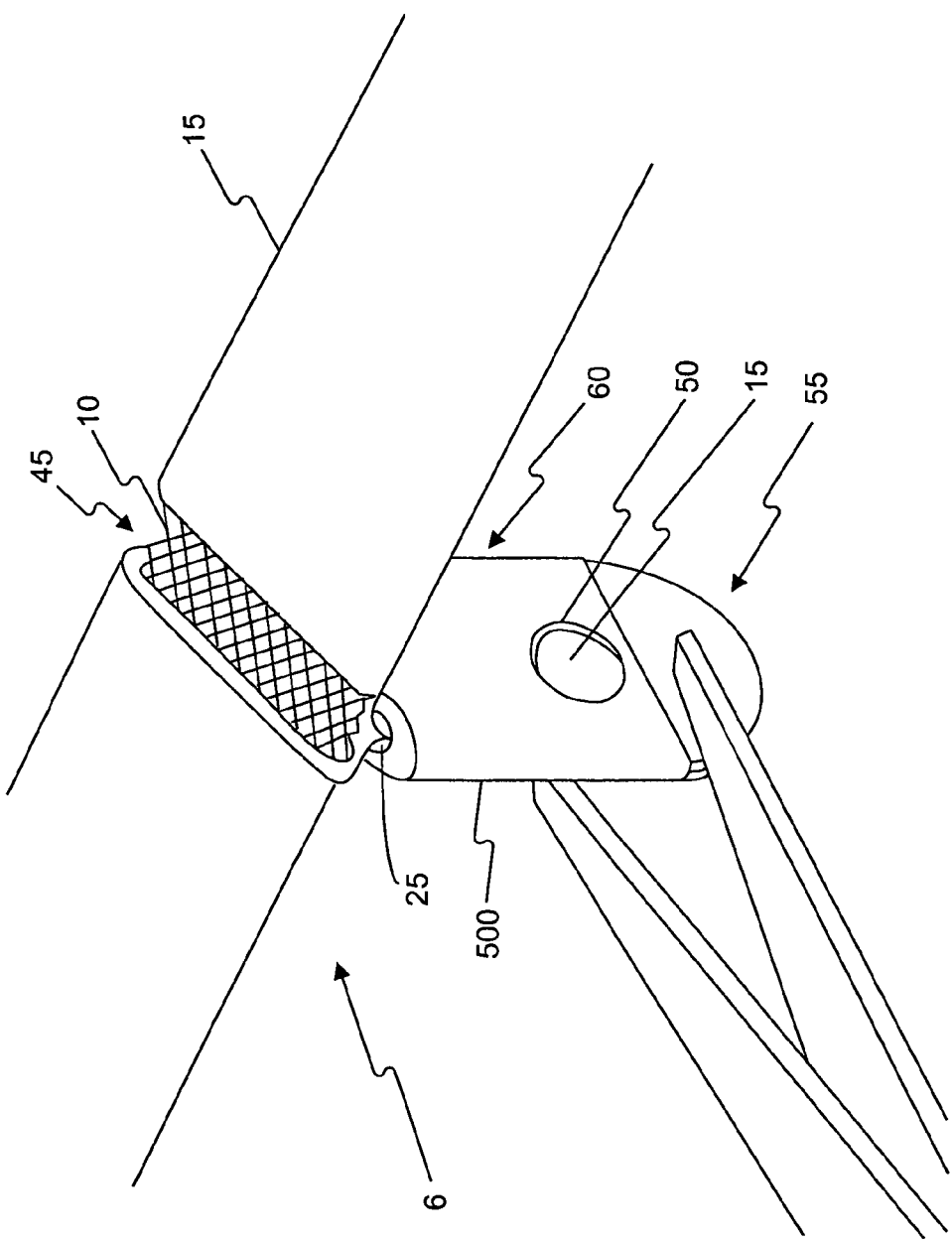
FIG. 13 is an elevation view of a current medical device and its positioning assembly.
Figure 14:
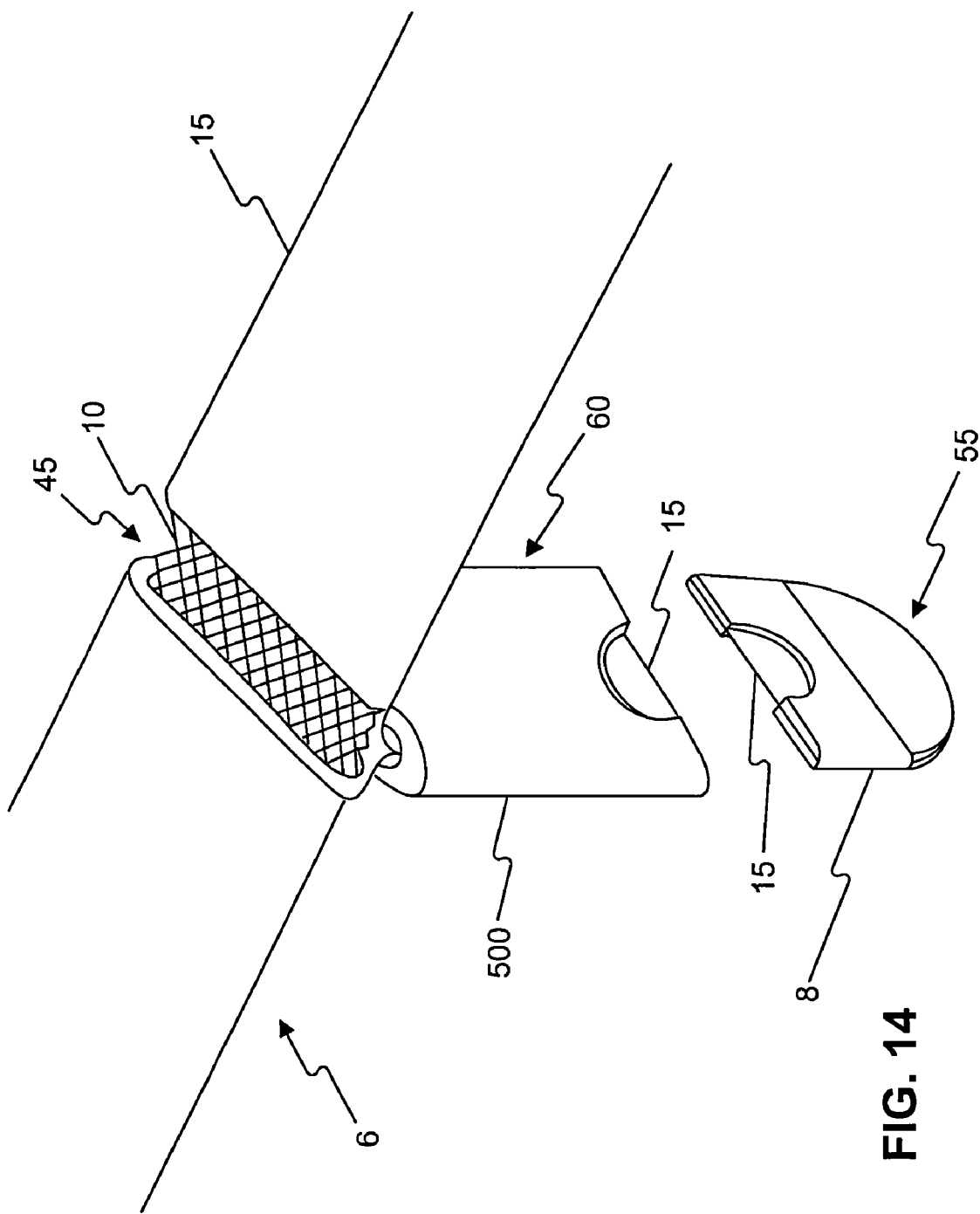
FIG. 14 is an elevation view of the medical device and positioning assembly of FIG. 13, showing a severed centering tab.

Once the centering tab 100 has been appropriately positioned, the physician may sever the centering tab 100 along a longitudinal axis 57 of the centering tab 100, as shown in FIGS. 11 and 12. Severing the centering tab 100 along the longitudinal axis 57, or otherwise along the length of portion 55 of tab 100, may also sever the single layer 30 of the sleeve 15 disposed along the proximal portion 55 of the centering tab 100. The severed centering tab 100 and single layer 30 are illustrated in FIG. 12. Although the centering tab 100 has been severed, the centering tab 100 may remain a one-piece device. The severed centering tab 100 may be removed from the body of the patient by manipulating the centering tab 100 in the direction of arrow 150 shown in FIG. 12.

As discussed above, severing the centering tab 100 also facilitates the removal of the sleeve 15 from the body while leaving the mesh 10 appropriately positioned relative to the urethra 130. For example, manipulating the distal ends 135 of the sleeve 15 (FIG. 10) in the direction of arrows 140, after severing the centering tab 100 and the sleeve 15, may remove the sleeve 15 from the body of the patient while leaving the mesh 10 positioned beneath and proximate the urethra 130. Such manipulation may be facilitated by the tubes 12 (FIG. 1A). When appropriately positioned, the mesh 10 may contact the urethra 130 of the patient. This contact may support at least a portion of the urethra 130 in times of heightened stress or increased intra-abdominal pressure.

Appropriately positioning the mesh 10 relative to the urethra 130 may also include positioning the center portion 45 of the mesh 10 proximate the urethra 130 such that the rounded edges 47 (FIG. 2B) of the center portion 45 may be proximate the urethra 130. As described above, manipulating the centering tab 100 may cause a corresponding movement of the sleeve 15 and the mesh 10 disposed therein. Any suitable manipulation technique may be used. For example, in an embodiment such as the embodiment shown in FIGS. 5 and 6, positioning the medical device positioning assembly 5 may also include manipulating at least one of the protrusions 90 located on the distal portion 60 of the centering tab 200. During use, the centering tab 200 may be positioned, severed, and removed in substantially the same way as described above with respect to centering tab 100.

Similar to the centering tabs 100, 200, the centering tab 300 of the embodiment of FIGS. 7 and 8 may also be severed along a longitudinal axis 57, or otherwise along the length of tab 300, to facilitate removal of the centering tab 300 and the sleeve 15 from the body of the patient. Severing the centering tab 300 along axis 57 also severs the sleeve 15 and results in a one-piece tab for removal from the patient.

Accordingly, severing the centering tabs of the present disclosure so as to maintain a one-piece configuration may improve the safety of the surgical procedure. The severing process does not create additional pieces of material and does not reduce the size of the centering tab, so that the tab is simple to grasp, manipulate, and/or remove after being severed.

Other embodiments of the invention will be apparent to those skilled in the art from consideration of the specification and practice of the invention disclosed herein. For example, each of the centering tabs disclosed herein may further include a textured surface, such as along a portion of the distal portion 60 of the centering tab. The textured surface may assist in gripping the centering tab. In further embodiments, at least a portion of at least one of the sides of the proximal portion of the centering tab 100 may be removed. The removal of material from the centering tab 100 may result in a centering tab 100 that is more flexible and easier to sever.

It is intended that the specification and examples be considered as exemplary only, with a true scope and spirit of the invention being indicated by the following claims.

What is claimed is:

1. An assembly for positioning a medical device, comprising:
 a sleeve having a lumen configured to accept a medical device;
 a tab including a distal portion and a proximal portion, the distal portion comprising a channel configured to receive a portion of the sleeve that does not include the medical device, the proximal portion comprising an outer surface;
 wherein the sleeve extends around the outer surface of the proximal portion of the tab; and
 wherein the tab is configured such that completely severing the tab along its longitudinal axis severs the sleeve into two unconnected pieces and maintains the tab in one piece.

2. The assembly of claim 1, wherein a portion of the sleeve has a single layer without a lumen.

3. The assembly of claim 2, wherein severing the tab along a length of the tab severs the single layer of the sleeve.

4. The assembly of claim 1, wherein the medical device is a mesh.

5. The assembly of claim 4, wherein the mesh is configured to remain substantially stationary relative to the sleeve.

6. The assembly of claim 4, wherein a center portion of the mesh is positioned proximate the tab.

7. The assembly of claim 6, wherein the center portion of the mesh includes substantially atraumatic edges.

8. The assembly of claim 4, wherein the tab is configured to assist in positioning the mesh within the body of a patient.

9. The assembly of claim 8, wherein positioning the sleeve causes a corresponding positioning of the mesh.

10. The assembly of claim 1, wherein the distal portion of the tab defines a channel configured to receive the sleeve.

11. The assembly of claim 10, wherein the sleeve extends from the channel through a first orifice of the tab.

12. The assembly of claim 11, wherein the sleeve extends from the channel through a second orifice of the tab.

13. The assembly of claim 10, wherein the channel includes an opening at a distal end of the tab.

14. The assembly of claim 13, wherein the opening at the distal end of the tab receives the sleeve.

15. The assembly of claim 1, wherein the tab includes a protrusion on the distal portion of the tab and configured to assist in positioning the tab.

16. The assembly of claim 1, wherein the proximal portion has a substantially cylindrical shape.

17. The assembly of claim 1, wherein the sleeve is connected to the tab at the distal portion.

18. A method of implanting a medical device to support a urethra of a body, comprising:
 providing the medical device within a lumen of a sleeve;

providing a tab receiving the sleeve; positioning the sleeve and the medical device beneath the urethra;

positioning a portion of the mesh beneath the urethra using the tab;

severing a proximal portion of the tab and the sleeve while maintaining the tab in one piece wherein the sleeve extends along an outer surface of the proximal portion of the tab; and removing the tab and the sleeve from the body.

19. The method of claim 18, wherein severing the tab includes cutting the tab along a length of the tab.

20. The method of claim 18, wherein severing the tab assists in the removal of the tab and the sleeve.

21. The method of claim 18, wherein the proximal portion has a substantially cylindrical shape.

22. The method of claim 18, wherein removing the tab and the sleeve includes manipulating the tab in a first direction and manipulating the sleeve in a second direction substantially opposite the first direction.

23. The method of claim 18, wherein the medical device is a mesh.

24. The method of claim 18, wherein a distal portion of the tab defines a channel configured to receive the sleeve.

25. The method of claim 24, wherein the sleeve extends from the channel through a first orifice of the tab.

26. The method of claim 25, wherein the sleeve extends from the channel through a second orifice of the tab.

27. The method of claim 24, wherein the channel includes an opening at a distal end of the tab.

* * * * *